United States Patent [19]

Jung et al.

[11] Patent Number: 5,141,739

[45] Date of Patent: Aug. 25, 1992

US005141739A

[54] DELIVERY OF X-RAY CONTRAST AGENTS USING RECEPTOR MEDIATED ENDOCYTOSIS

[75] Inventors: Chu Jung, Arlington; Stephen Palmacci, Walpole; Lee Josephson, Arlington, all of Mass.

[73] Assignee: Advanced Magnetics, Inc., Cambridge, Mass.

[21] Appl. No.: 679,526

[22] Filed: Apr. 2, 1991

Related U.S. Application Data

[63] Continuation-in-part of Ser. No. 384,991, Jul. 28, 1989, abandoned, which is a continuation-in-part of Ser. No. 228,640, Aug. 4, 1988, abandoned, which is a continuation-in-part of Ser. No. 67,586, Jun. 26, 1987, Pat. No. 4,827,945, which is a continuation-in-part of Ser. No. 882,044, Jul. 3, 1986, Pat. No. 4,770,183.

[51] Int. Cl.$^5$ .................. A61K 49/04; A61K 31/715; A61K 31/02; A61K 31/025

[52] U.S. Cl. ........................ 424/4; 424/1.1; 424/5; 514/54; 514/57; 514/60; 514/950; 514/743; 514/747

[58] Field of Search ............ 424/4, 5, 1.1; 514/54, 514/57, 60, 950, 743, 747

[56] References Cited

U.S. PATENT DOCUMENTS

| | | | |
|---|---|---|---|
| 3,852,413 | 12/1974 | Cammarata | 424/1.1 |
| 4,069,306 | 1/1978 | Rothman | 424/4 |
| 4,243,653 | 1/1981 | Sovak et al. | 424/5 |
| 4,431,626 | 2/1984 | Henze | 424/1.1 |
| 4,501,726 | 2/1985 | Schroder et al. | 424/1.1 |
| 4,618,492 | 10/1986 | Blattler et al. | 424/85 |
| 4,675,173 | 6/1987 | Widder | 424/9 |
| 4,744,760 | 5/1988 | Molday | 424/3 |
| 4,770,183 | 9/1988 | Groman et al. | 128/654 |
| 4,804,529 | 2/1989 | Bardy et al. | 424/9 |
| 4,822,594 | 4/1989 | Gibby | 424/9 |
| 4,827,945 | 5/1989 | Groman et al. | 128/653 |
| 4,859,449 | 8/1989 | Mattes | 424/9 |
| 5,066,789 | 11/1991 | Srinivasan et al. | 530/388 |

FOREIGN PATENT DOCUMENTS

| | | |
|---|---|---|
| 83964 | 7/1983 | European Pat. Off. |
| 186947 | 7/1986 | European Pat. Off. |
| 9001295 | 2/1990 | PCT Int'l Appl. |
| 9003190 | 4/1990 | PCT Int'l Appl. |
| 973881 | 10/1964 | United Kingdom |

OTHER PUBLICATIONS

Fischer, H. W. (1990) Invest. Radiol. 25 Suppl. 1, pp. S2-S6.
Gennaro, A. R. et al., "Remington's Pharmaceutical Sciences," Eighteenth Edition, 1990, pp. 817-823.
Glicksman, ed. "Food Hydrocolloids," CRC Press, Inc., Boca Raton, Fla., 1982, pp. 5 and 33.
Goresky and Schwab in "The Liver: Biology and Pathobiology," I. M. Arias et al., eds., 2nd Ed., Raven Press, N.Y., 1988, Chapter 46.
Gorin and Barreto-Bergter in "The Polysaccharides," G. O. Aspinall, ed., vol. 2, Academic Press, N.Y., 1983, pp. 376-380.
Harford and Ashwell in "The Glycoconjugates" vol. IV, M. I. Horowitz, ed., Academic Press, N.Y., 1982, pp. 27-55.
Josephson et al. (1990) Mag. Res. Imag. 8 pp. 637-646.
Katayama, H. (1990) Invest. Radiol. 25, Suppl. 1, pp. S7-S10.
Stockert and Becker (1980) Cancer Res. 40 pp. 3632-3634.
Wileman et al. (1985) Biochem. J. 232 pp. 1-14.

Primary Examiner—Richard L. Raymond
Assistant Examiner—Gary E. Hollinden
Attorney, Agent, or Firm—Bromberg & Sunstein

[57] ABSTRACT

The invention provides a method of targeting an x-ray contrast agent to a specific population of cells or organ. Targeting may be accomplished by forming a complex of a radiopaque label with a saccharide capable of interacting with a cell receptor. The resulting complex may then be internalized into the specific population of cells or organ by receptor mediated endocytosis. In one embodiment of the invention, the radiopaque label may include a compound containing iodine and the saccharide may include arabinogalactan, galactan, or derivatives thereof. The invention provides a method for determining the metabolic viability or disease state of the target cells or organ by visualizing the extent, mode of uptake and excretion of the targeted x-ray contrast agent by x-ray or computer tomography.

18 Claims, 1 Drawing Sheet

DELIVERY OF X-RAY CONTRAST AGENTS USING RECEPTOR MEDIATED ENDOCYTOSIS

CROSS REFERENCE TO RELATED APPLICATION

This application is a continuation-in-part of U.S. application Ser. No. 07/384,991, filed Jul. 28, 1989, now abandoned which is a continuation-in-part of U.S. application Ser. No. 07/228,640, filed Aug. 4, 1988, now abandoned, which is a continuation-in-part of U.S. application Ser. No. 07/067,586, filed Jun. 26, 1987, now U.S. Pat. No. 4,827,945, which is, in turn, a continuation-in-part of U.S. application Ser. No. 06/882,044, filed Jul. 3, 1986, now U.S. Pat. No. 4,770,183. These related applications are hereby incorporated herein by reference.

TECHNICAL FIELD

The present invention relates to methods for the delivery of x-ray contrast agents and radiological compositions containing such agents to a specific population of cells or an organ, such as the liver.

BACKGROUND ART

A. Conventional X-ray Contrast Agents

An x-ray contrast agent is administered for the purpose of visualizing physiological structures or functions with x-rays or computer tomography (CT). X-ray contrast agents may be comprised of complex molecules containing electron dense labels. Conventional x-ray contrast agents in general use are composed of iodine, which provides opacification to the x-rays, which is attached to an aromatic nucleus, which provides a high degree of stability required for pharmacological inertness. This basic aryl iodide unit may be modified by various chemical groups in order to provide the necessary high water solubility, in vivo stability, selective excretion and low viscosity and to minimize adverse side effects, such as osmotic or cytotoxic side effects.

Conventional x-ray contrast agents may include intravascular or targeted contrast agents. Intravascular agents are currently widely used and are non-selective. The few targeted x-ray contrast agents currently known are predominantly designed for targeting the fixed macrophages of the reticuloendothelial system (RES), in particular, the Kupffer cells for liver imaging.

B. Intravascular X-ray Contrast Agents

Conventional, intravascular x-ray contrast agents are generally used to opacify the vascular space or extracellular (interstitial) space. Examples of intravascular contrast agents include salts of metrizoic acid [3-acetamido-5-(N-acetylmethylamino)-2,4,6-triiodobenzoic acid; FIG. 1, $R_1 = -COOH$, $R_2 = -NHC(O)CH_3$, $R_3 = -N(CH_3)C(O)CH_3$, British Patent 973881 (1964)]; diatrizoic acid ($R_1 = -COOH$, $R_2 = R_3 = -NHC(O)CH_3$); and low-osmolality, non-ionic contrast agents such as ioversol [N,N'-bis(2,3-dihydroxypropyl)-5-[(hydroxyacetyl)(2-hydroxyethyl)amino]-2,4,6-triiodo-1,3-benzenedicarboxamide; $R_1 = R_2 = -C(O)NHCH_2CH(OH)CH_2OH$, $R_3 = -N(CH_2CH_2OH)(C(O)CH_2OH)$; Lin, Y., European Patent Application Ser. No. 83,964, filed Jan. 5, 1983, published Jul. 20, 1983].

The degree of enhancement of the images of organs other than the brain and kidneys with these intravascular and extracellular x-ray contrast agents is highly time dependent. The pharmacokinetics of these conventional x-ray contrast agents must be carefully considered and the x-ray or CT scans closely synchronized with the administration of the contrast agent in order to obtain meaningful diagnostic data. Intravenous bolus injection or infusion of these contrast agents results in rapid dilution of the contrast agent by vascular mixing, diffusion of the contrast agent from the capillary network into the interstitial or extracellular space, and renal excretion. This initial vascular phase lasts only 1-2 min in the case of a bolus injection, or the duration of the infusion. Initial concentrations of contrast agent are much higher with an injection (bolus effect; <1 min duration). As the blood concentration of the contrast agent falls below that in the interstitial space, the contrast agent diffuses back into the vascular space (parenchyma phase) where it will undergo continued renal excretion. These conventional, intravascular x-ray contrast agents are very useful for imaging vascular (angiography) and renal (urography) structures.

With these intravascular contrast agents, enhanced tissue contrast is due primarily to differences in tissue vascularity. Consequently, maximum contrast enhancement in body tissues occurs during the short 1-2 min period of the vascular phase with a bolus injection. Enhanced tissue differentiation can occur during the parenchyma phase due to differences in the relative interstitial volumes of normal and pathological tissue, however, with the exception of brain and kidney x-ray or CT scans, these differences are small. In general, CT scans must be performed within the short vascular phase in order not to miss a diagnosis. The time required for the contrast agent to reach the target region of interest from the injection site (circulation time) must also be factored into the synchronization of the x-ray or CT exam.

C. Liver Computer Tomography

The majority of hepatic metastatic tumors are hypovascular relative to normal liver parenchyma and appear isodense (i.e., no contrast) in CT scans. The hypovascular tumors will appear hypointense (darker) relative to the normal liver during 1-3 min after the start of a bolus injection of an intravascular x-ray contrast agent. After this initial period, the x-ray contrast agent washes out of the normal liver tissue, while its concentration increases in the hypovascular tumor. This situation may result in even less contrast than present in the unenhanced CT scan. In general, this model also applies to other hypovascular pathological tissue (cysts, tumors, abscesses, necrosis, infarction and ischemia).

With hypervascular tumors, increased tissue contrast is obtained at approximately 30 sec after the start of the bolus injection of the contrast agent due to the fact that tumor perfusion occurs via the hepatic artery (circulation time 20 sec). During this time the tumor appears hyperintense (brighter) relative to liver parenchyma which relies on the portal venous circulation (circulation time 35 sec). This enhancement is short-lived (~1 min) as the contrast agent quickly washes out of the hypervascular tumor and washes into the normal liver via the portal venous circulation. In this case, the timing of the dynamic CT scan is even more critical than with the majority of cases of hypovascular tumors. Both types of tumors appear isointense in CT scans during the parenchyma phase (3-5 min post-injection). Slow infusion of intravascular contrast agents is of no diagnostic value for the detection of focal liver tumors.

The short temporal contrast enhancement characteristic of intravascular contrast agents is due to the fact that they do not exhibit any organ or tissue specificity. Image contrast enhancement with these conventional, non-specific contrast agents is due to differences in tissue vascularity (blood flow and capillary bed volume) and relative interstitial volumes. Due to their rapid dilution in the blood stream, large doses (for body CT scans: 7 to 60+ g of organically bound iodine) of conventional intravascular contrast agents are required in order to obtain sufficiently large concentrations in the region of interest. These large doses can produce severe side reactions; over dosages are life threatening. Low osmolality contrast agents were developed in an attempt to minimize these adverse reactions (H. Katayama, Invest. Radiol., 25, Suppl. 1, S7–S10, 1990).

D. Conventional Targeted Liver Contrast Agents

Previous attempts to develop targeted x-ray contrast agent for liver opacification involved the use of particulate agents such as thorium dioxide and emulsions such as radiopaque liposomes, EOE-13 (iodinated esters of poppy seed oil) and PFOB (perfluoroctylbromide) (H. W. Fischer, Invest. Radiol., 25, Suppl. 1, S2–S6, 1990). These agents are filtered from the blood stream by the fixed macrophages of the reticuloendothelial system (RES). Accumulation of these radiopaque agents in the liver by the Kupffer cells, which constitute only 2–3% of the liver parenchyma, produced selective opacification of normal liver tissue as Kupffer cells are absent in pathological tissue such as tumors. These agents are not in general use due to high toxicity and/or high incidences of severe side effects. Radioactive thorium dioxide does not clear from the liver and produces liver and spleen neoplasms and fibrosis.

Radiopaque liposomes obtained by encapsulation of intravascular x-ray contrast agents (e.g. diatrizoate) have been hampered by low encapsulation efficiency, "leakiness," broad size distributions and insufficient liver opacification. Sterilization of the radiological compositions of these liposomes is also complicated by the inherent instability of the liposome structure (e.g. no heat sterilization).

EOE-13 is rapidly cleared from the blood stream (95% of dose in 5 min) by the liver and spleen and is efficiently eliminated by renal excretion of its metabolic by-products (including free iodine). While it was efficient in opacifying the liver and spleen, it showed little contrast enhancement of hepatic and splenic tumors. EOE-13 also produced a relatively high incidence (4%) of severe adverse reactions.

PFOB is very slowly cleared from the vascular space by the RES of the liver and spleen and by the lungs and resulted in enhanced vascular structures for >3 hours post-injection; after 2 hours, PFOB showed more spleen than liver opacification. It behaved similarly to EOE-13 as hepatic or splenic lesions showed minimal contrast enhancement. A unique drawback to the clinical application of this perfluorocarbon is the ecological impact of its continued manufacture and disposal. The destruction of the atmospheric ozone layer by fluorocarbons has led to the development of alternatives to these chemicals in other applications. This current trend away from fluorocarbons may have adverse effects on the price and availability of PFOB.

Alternately, liver x-ray contrast agents may be targeted toward the hepatocytes which constitute approximately 97% of the liver parenchyma. Current hepatocyte directed (non-RES) x-ray contrast agents are the cholecystographic (oral) or cholangiographic (intravascular) agents used primarily for gall bladder opacification. These agents are triiodinated aryl compounds with a hydrophobic site on the aromatic nucleus. They show high serum albumin binding (noncovalent) and are cleared from the vascular system by the hepatocytes. The low concentrations of free cholecystographic agents in the blood stream minimizes their vascular extraction by the renal system. Transport of these small molecules across the hepatocyte plasma membrane occurs by a carrier-mediated membrane transport mechanism (C. A. Goresky and A. J. Schwab, The Liver, Biology and Pathobiology, I. M. Arias, ed., 2nd Ed., 1988, chapter 46). Subsequent hepatobiliary excretion and concentration in the gall bladder results in enhanced images of the gall bladder. Little enhancement of the liver is obtained with cholecystographic agents due to their slow absorption from the intestines and low vascular and hepatic concentrations. Cholangiographic agents also show little liver enhancement due to rapid hepatobiliary excretion and are not as widely used due to higher toxicities which are attributable to their high affinities for blood plasma proteins.

E. Receptor Mediated Endocytosis (RME)

RME is a process whereby macromolecules in the extracellular space bind to specific receptors on the cell surface and are internalized by pinching-off of the cell membrane to form intracellular vesicles. Macromolecules injected into the vascular compartment are cleared (removed) from plasma by this RME process. RME differs from carrier-mediated membrane transport systems, which facilitates movement of small molecules across cell membranes.

Uptake by RME exhibits three general properties characteristic of ligand-receptor interactions generally: structural specificity, saturability and competition. Structural specificity is observed when a receptor can distinguish between closely related structures and only molecules with structures meeting the binding requirements of the receptor binding site are internalized. Often the receptors involved in RME are discovered by their ability to internalize or clear glycoproteins from circulation. Saturability is observed when the rate of an agent internalized via RME decreases with increasing concentrations of that agent. This effect is due to the fact that at high concentrations the receptor approaches full occupancy or becomes saturated with the ligand.

Competition is observed when the rate of internalization of an agent can be reduced by the presence of additional agents bearing a structural resemblance to the first agent. The additional agents compete for receptor binding sites and decrease the rate of internalization of the first agent. Saturability results when high concentrations of a single ligand compete for a limited number of receptor sites. Competition results when chemically different ligands bind to a limited number of receptor sites.

The uptake of substances by RME is a feature of normal, healthy cells. RME transport systems can be found on normal macrophages, hepatocytes, fibroblasts, and reticulocytes. RME enables cells to internalize a variety of macromolecules in plasma, such as asialoglycoproteins, low density lipoproteins, transferrin, and insulin. See Tables 1 in Wileman et al., Biochem. J., 232, 1-14, 1985 and Menz, E. T., et al., International Application published under the Patent Cooperation Treaty, International Publication No. WO 90/01295, filed Aug. 3, 1989, published Feb. 22, 1990, for a list of cells performing RME. The former reference is also a general review of RME. Conversion of normal cells to tumor cells (transformation) may be associated with an increase or decrease in the activity of receptors performing RME. In some cases, such as the RME performed by the asialoglycoprotein receptor of hepatocytes, transformation to cancerous hepatoma cells is associated with receptor loss (Stockert and Becker, Cancer Res. 40, 3632-3634, 1980). In many cases, like the antibody based targeting of drugs to tumor antigens, the antigens are increased on tumor cells and decreased on normal cells.

Monosaccharides and polysaccharides such as mannose and arabinogalactan, respectively, which interact with receptors involved in RME are referred to below as RME-type monosaccharides or polysaccharides. Many common monosaccharides or polysaccharides such as glucose, dextrans, dextrins, celluloses, hydroxyethyl starches, heparins, starches, dextran sulfates, carboxylmethylated dextran and carboxymethyl cellulose do not interact with receptors involved in RME; they are referred to below as non-RME monosaccharides or polysaccharides.

Non-RME type polysaccharides have been used in the synthesis of a variety of materials used as diagnostic or therapeutic agents (Jacobsen, T., European Patent application Ser. No. 186,947, filed Oct. 25, 1985, published Jul. 9, 1986; Schroder, U.S. Pat. No. 4,501,726; Ranney, D. F., International Application published under the Patent Cooperation Treaty, International Publication No. WO 90/03190, filed Sep. 29, 1989, published Apr. 5, 1990; Groman, U.S. Pat. No. 4,827,945; Groman, U.S. Pat. No. 4,770,183). Ranney discloses the delivery of diagnostic agents (metal ions as magnetic resonance (MR) contrast agents), using a polymeric carrier which is directed to tumor cells. Ranney suggests, without detailed examples, that other therapeutic complexes may also be delivered using this method for chemotherapeutic impact or to provide sensitization or augmentation for radiation treatment. Ranney, D. F., International Application published under the Patent Cooperation Treaty, International Publication No. WO 90/03190, filed Sep. 29, 1989, published Apr. 5, 1990, page 51. However, Ranney does not disclose the use of RME-type saccharides, nor the binding of electron dense organic compounds. It is known that the RME-type polysaccharide arabinogalactan can be used to target a variety of diagnostic agents, particularly superparamagnetic iron oxide. Menz, E. T., et al., International Application published under the Patent Cooperation Treaty, International Publication No. WO 90/01295, filed Aug. 3, 1989, published Feb. 22, 1990.

SUMMARY OF THE INVENTION

The present invention provides a method of targeting an x-ray contrast agent to a specific population of cells or organ. Targeting may be accomplished by forming a complex of a radiopaque label with a saccharide capable of interacting with a cell receptor. The resulting complex may then be internalized into the specific population of cells or organ by receptor mediated endocytosis. In one embodiment of the invention, the radiopaque label may include a compound containing iodine and the saccharide may include arabinogalactan, galactan, or derivatives thereof. The invention provides a method for determining the metabolic viability or disease state of the target cells or organ by visualizing the extent, mode of uptake and excretion of the targeted x-ray contrast agent by x-ray or computer tomography.

BRIEF DESCRIPTIONS OF THE FIGURES

The foregoing features of the invention will be more readily understood by reference to the following detailed description taken with the accompanying drawing, in which:

FIG. 1 illustrates the structure of conventional x-ray contrast agents.

DETAILED DESCRIPTION OF SPECIFIC EMBODIMENTS

A. General

Figure 1:
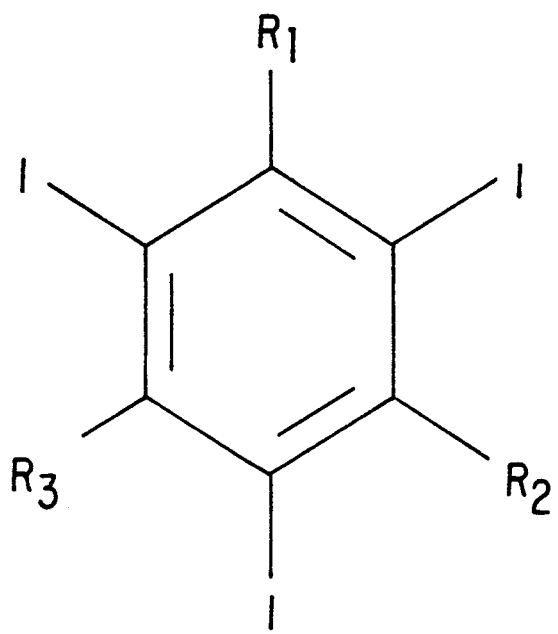

The invention provides a method of targeting x-ray contrast agents and radiological compositions containing such agents to a specific population of cells or organ. Targeting is the modification of an agent so that after parenteral administration its uptake by a specific type or population of cells is increased, over that obtained with the unmodified agent. Targeting may be accomplished by forming a complex between a radiopaque label and a saccharide capable of interacting with a cell receptor (an RME-type saccharide). The resulting complex may then be allowed to enter the specific population of cells by receptor mediated endocytosis.

The invention is specifically directed to RME-type saccharides, which are saccharides capable of receptor mediated endocytosis, including RME-type monosaccharides and polysaccharides, such as arabinogalactan, galactose and mannose, as well as derivatives and degradation products thereof. According to the methods of the invention, a complex of an RME-type saccharide and a radiopaque diagnostic label may be formed and delivered to a specific population of cells by receptor mediated endocytosis. The radiopaque label may include a composition containing iodine, such as a polyiodinated aromatic group or a polyiodinated aliphatic group. Radiopaque labels that may be delivered to a specific population of cells according to the methods of the invention include ioversol, metrizoic acid and 3-amino-2,4,6-triiodobenzoic acid.

In particular, the present invention provides a method of targeting an x-ray contrast agent to the hepatocytes or Kupffer cells (non-RES uptake) of the liver, which have cell receptors for galactose or mannose, respectively. The targeting of x-ray contrast agents, according to the methods of the invention, provides a method of increasing the concentration of the x-ray contrast agent in organs or tissues, where it can opacify the regions to be examined by x-ray or CT, and reducing its concentration in other organs or tissues, where unwanted, toxic effects would be produced. In addition, according to the methods of the invention, smaller doses of a targeted x-ray contrast agent would be required, since dilution in the vascular space would not result in decreased opacification of the target organ. The pharmacokinetics of the targeted x-ray contrast agents of the invention may enable longer, more detailed x-ray or CT examinations of organs than is currently possible with conventional intravascular x-ray contrast agents and would be eliminated from the body after the x-ray or CT scan. This property would eliminate the crucial need for accurate synchronization of contrast agent administration and x-ray or CT scanning. Inaccurate synchronization of intravascular contrast agent injection and CT scanning results in misdiagnosis, or requires repetition of the procedure. The former may result in dire health consequences for the patient, while the latter will subject the patient to undesirable, higher doses of contrast agent and x-rays. The invention may also be directed to the use of targeted contrast agents in non-radiographic procedures including CT scans of the bile ducts and gall bladder and ultrasonic scans.

In a further embodiment of the invention, extraction of the x-ray contrast agents from the blood stream by the targeted organ or tissue would provide a means of visualizing the metabolic or functional viability (disease state) of the target tissue with an x-ray or CT scan. Since the biodistribution of RME-directed x-ray contrast agents is different from that of conventional intravascular or RES-directed x-ray contrast agents, the use of the contrast agents of the present invention provides superior differentiation (i.e. enhanced image contrast) of anatomical details between different organs, or different tissue compartments of the same organ in x-ray or CT scans.

In accordance with the present invention, radiological compositions may be prepared that include an x-ray contrast agent and a pharmaceutically acceptable radiological vehicle. Pharmaceutically acceptable radiological vehicles include those that are suitable for injection such as aqueous buffer solutions; e.g. phosphate, citrate, bicarbonate, etc., sterile water for injection, physiological saline and balanced ionic solutions containing chloride and/or bicarbonate salts of normal blood plasma cations such as Ca, Na, K and Mg. Gennaro, A. R. et al. "Remington's Pharmaceutical Sciences," Eighteenth Edition, 1990, pp. 817–823. The radiological composition is administered so that the contrast agent remains in the living animal body for about 1 to 3 hours, although both shorter and longer residence periods are normally acceptable.

B. Advantages of Polysaccharides as Carriers for the Delivery of X-ray Contrast Agents An advantage of using polysaccharides instead of proteins for the delivery of x-ray contrast agents is that polysaccharides do not denature readily at high temperature (enabling sterilization by the application of heat), extremes of pH or in organic solvents. Because of the stability of polysaccharides, covalent linkages between x-ray contrast agents and polysaccharides may be achieved in organic solvents. This is a considerable advantage since some x-ray contrast agents have low water solubility. A related advantage of the solubility of polysaccharides in nonaqueous media is that water unstable linkages such as esters may be created between the x-ray contrast agent and the polysaccharide. An example of such chemistry is provided by Example 1.

Another advantage of polysaccharides is that they can be obtained from microbiological or plant sources. Glycoproteins from human or animal sources may contain pathogens whose absence is costly to assure. Polysaccharides from microbiological or plant sources may be selected for use in the invention, which are very low toxicity in immunogenicity. Plant or microbiological sources may provide crude polysaccharide preparations on a large scale, in a reliable manner and at a reasonable price. Two classes of carbohydrates which may be utilized in the invention are the arabinogalactans and the mannans.

C. Arabinogalactans

Arabinogalactans are a class of polysaccharides that may be obtained from the cell walls of many species of trees and plants. Arabinogalactan binds to the asialoglycoprotein receptor of hepatocytes. A common source of arabinogalactan is the American western larch (Larix occidentalis). Arabinogalactan from this source is used as a binder, emulsifier or stabilizer in foods. It consists of a galactose backbone with branch chains of arabinoses and galactose. Generally the ratio of galactose to arabinose is between 5 to 1 and 10 to 1. The molecular weight may be between 10 to 100 kilodaltons. "Food Hydrocolloids," Glicksman, ed., CRC Press, 1982, p. 5 and p. 33.

Best results are obtained when a purified arabinogalactan is used. Commercially available arabinogalactan may be further purified by ultrafiltration to remove impurities greater than 100,000 daltons and smaller than about 3,000 daltons. Arabinogalactan purified by this method is utilized in the examples of the patent.

Arabinogalactans bind to the asialoglycoprotein receptor of hepatocytes. This receptor performs RME on a variety of substances (Harford and Ashwell in "The Glycoconjugates, vol. IV, M. I. Horowitz, Ed., Academic Press, 1982 pp. 27–55). X-ray contrast agents attached to arabinogalactan will be targeted to hepatocytes.

D. Mannans

Mannans are a class of polysaccharides that can be obtained from the cells walls of yeasts. They can bind to the mannose receptor on phagocytic cells of many species. They are predominantly alpha-D-mannopyrans with a variety of linear and branched chain structures. P. A. J. Gorin and E. Barreto-Bergter, "The Polysaccharides," G. O. Aspinall, ed., vol. 2 Academic Press, 1983, pp. 376–380.

Mannans bind to the mannose receptor found on the macrophages of the RES. X-ray contrast agents attached to mannan will be targeted to macrophages.

E. Distinguishing the RME-type Monosaccharides and Polysaccharides Used by the Invention With the current invention, an x-ray contrast agent may be attached to a monosaccharide or polysaccharide and the resulting complex may be targeted into specific types of cells through the action of cell surface receptors. Only certain monosaccharides or polysaccharides may be used in the invention and these are termed RME-type monosaccharides or polysaccharides (RME-type saccharides). RME-type saccharides differ from common, non-RME saccharides, e.g. dextrans, dextrins, celluloses, hydroxyethylstarches, heparins, starches, dextran sulfates, carboxylmethylated dextran and carboxymethyl cellulose. Non-RME polysaccharides are used in diverse applications such as drug delivery, drug formulation, food additives and in plasma volume expansion. RME-type polysaccharides include arabinogalactan and mannan and derivatives thereof and may be used, according to the methods of the invention, to deliver x-ray contrast agents directly to hepatocytes and macrophages, respectively. RME-type monosaccharides include galactose, which is recognized by the asialoglycoprotein receptor present on hepatocytes and mannose which is recognized by its receptor on macrophages.

We below refer to the complexes of the invention as the RME-type saccharide/x-ray contrast agent complex. The complex between the RME-type saccharide and the x-ray contrast agent may involve the covalent attachment of the radiopaque label to the RME-type saccharide directly, or via a linking group which includes polycarboxylic acids, polyaminocarboxylic acids, polyamines, and aminoalkanols.

Chemical modifications of non-RME polysaccharides have been achieved, including carboxymethylation, succinylation, hydroxyethylation, and sulfation. Generally, such chemical modification of common polysaccharides does not confer the ability to bind to a receptor and undergo RME. However, non-RME polysaccharides may in some instances be modified by the attachment of substituent groups that are recognized by receptors performing RME, and such modifications confers the property of RME on non-RME polysaccharides. For example, a galactose residue can be attached to the non-RME polysaccharide dextran, allowing the galactose of the resulting polysaccharide to be recognized by the asialoglycoprotein receptor and to undergo RME. By attachment of galactose, the dextran is converted into an RME-type polysaccharide. Similarly, a mannose group may be attached to dextran and the resulting polysaccharide will be recognized by the mannose receptor of phagocytes. Synthetic polymers obtained by polymerizing carbohydrate molecules with the aid of bifunctional coupling or cross-linking agents may also be modified in this manner.

A second modification of RME type polysaccharides involves partial digestion to produce lower molecular weight polysaccharides, which may considered derivatives thereof. This may be accomplished by controlled hydrolysis with acid and fractionation to obtain RME-type polysaccharides in the desired size class. The polysaccharides of the invention, before degradation or modification, have molecular weights greater than about 1,000 daltons.

For polysaccharides to be designated an RME-type polysaccharide its binding to a receptor performing RME must be demonstrated. One type of demonstration involves the ability of an RME-type polysaccharide to block the clearance of a glycoprotein known to be cleared by RME. For example, the interaction of arabinogalactan with the asialoglycoprotein receptor was demonstrated by its ability to block the clearance of a radioactive sample of the asialoglycoprotein, asialofetuin. Injection of 500 mg/kg of arabinogalactan blocks the clearance of $^{125}$I-asialofetuin in rats. (See Table 1 of Josephson et al., Mag. Res. Imag. 8:637–646; 1990.) As result of this experiment as well as others, it may be concluded that arabinogalactan is recognized by the asialoglycoprotein receptor of hepatocytes. Consequently arabinogalactan is an RME-type polysaccharide.

The clearance of the RME-type saccharide/x-ray contrast agent complexes of the invention is unaffected by the injections of substantial concentrations of non-RME type saccharides, e.g. dextran, hydroxyethyl starch. The clearance of the RME-saccharide/x-ray contrast agents of the invention is unaffected by the injection of substantial concentrations of particles, colloids or liposomes cleared by the phagocytic cells of the RES.

EXAMPLES

Example 1: Preparation of arabinogalactan-DTPA-ioversol

A. Preparation of arabinogalactan-DTPA:

Purified arabinogalactan (23,000 daltons, 20.0 g, 0.87 mmol) and diethylenetriaminepentaacetic acid dianhydride (2.15 g, 6.02 mmol) were dissolved in DMSO (200 mL) at 60° C. After 0.5 hour, the clear solution was added to H$_2$O (ca. 500 mL) at 15° C. A small aliquot (25 mL) of the aqueous solution was withdrawn for analysis. The remaining solution was filtered on Amicon YM3 and YM1 ultrafiltration membranes (5,000 and 1000 dalton cutoff, respectively) and washed with H$_2$O (2 . 400 mL). The solution (~70 mL) remaining on the membrane was frozen and lyophilized. Yield of white powder: 18.8 g.

The above aliquot (containing ~0.2 mmol DTPA) was neutralized with 0.1N NaOH and excess MnCl$_2$.4H$_2$O (70 mg, 0.35 mmol) was added. After readjusting the pH to 7.0, the solution was analyzed by HPLC on a Sephadex G-25 column (9.5×300 mm) with an eluent of 0.1% NaN$_3$ (0.33 mL/min) and a UV detector set at 280 nm. The chromatogram showed peaks with retention times of 16.4 and 23 min due to Mn$^{2+}$ coordinated to arabinogalactan-DPTA and free DPTA, respectively. Uncomplexed Mn$^{2+}$ appeared at 39 min. The relative areas of the arabinogalactan-[DPTA-Mn] and MnDTPA peaks indicated that 34% of the DPTA was conjugated to the arabinogalactan and corresponded to a molar ratio of DPTA:arabinogalactan of 2.4. This procedure was required as neither arabinogalactan-DPTA nor free DPTA absorbed at 280 nm. The presence of a large proportion of DMSO solvent precluded the use of a refractive index detector for assaying the degree of reaction.

B. Coupling ioversol to arabinogalactan-DTPA:

Arabinogalactan-DPTA (1.51 g, 0.53 meq —COOH) from above and solid ioversol (0.51 q, 0.63 mmol) were dissolved in DMSO (40 mL) at 60.C. 1-(3-dimethylaminopropyl)-3-ethylcarbodiimide hydrochloride (1.05 g, 5.88 mmol) was added and the reaction mixture was agitated at 60° C. for 28 hours, then cooled to ambient temperature and mixed with 50 mL H$_2$O. HPLC analysis using a Sephadex G-75 column (9.5×300 mm) with an eluent of 0.1% NaN$_3$ (0.33 mL/min) and a UV detector set at 280 nm indicated a 19% conjugation of the ioversol to the arabinogalactan-DPTA.

The solution was filtered on an Amicon YM3 ultrafiltration membrane (5,000 dalton cutoff) and washed with H$_2$O (3×30 mL). The retentate was frozen and lyophilized. Yield of off-white powder: 1.48 g.

Example 2: Preparation of arabinogalactan-DTPA-(3-amino-2,4,6-triiodobenzoic acid)

Arabinogalactan-DPTA (10.0 g, 5.2 meq —COOH, prepared as in Example 1, and 1-(3-dimethylaminopropyl)-3-ethylcarbodiimide hydrochloride (6.00 g, 33.6 mmol) were dissolved in DMSO (200 mL) at 60°–65° C. A solution of 3-amino-2,4,6-triiodobenzoic acid (3.0 g, 5.8 mmol) in DMSO (20 mL) was added over 5 min. The reaction mixture was stirred for 3 days at ambient temperature. HPLC analysis using a Sephadex (G-25 column (9.5×300 mm) with an eluent of 0.1% NaN$_3$ (0.33 mL/min) and a UV detector set at 280 nm indicated a 40% conjugation of the 3-amino-2,4,6-triiodobenzoic acid to the arabinogalactan-DPTA.

$H_2O$ (200 mL) was added and the solution purified by ultrafiltration using an Amicon YM3 membrane (5,000 dalton cutoff). The product remaining on the membrane was washed with 50% $DMSO/H_2O$ (2×200 mL) and $H_2O$ (2×300 mL). The product was then dissolved in $H_2O$ (200 mL), frozen and lyophilized. Yield of light-brown powder: 10 g.

Example 3: Preparation of
1-O-(2,3,5-triiodobenzyl)-4-O--
-D-galactopyranosyl-D-glucopyranoside A. Preparation of 2,3,5-triiodobenzyl alcohol:

2,3,5-triiodobenzoic acid (20 g, 40 mmol) is esterified with a $BF_3$-methanol (12 mL) complex in refluxing toluene (100 mL; 24 hours). The product methyl 2,3,5-triiodobenzoate was reduced with $LiBH_4$ (4.0 g, 0.18 mol) in refluxing diethyl ether (200 mL; 2 hours). This product is used in the synthesis of the following two carbohydrate derivatives.

B. Preparation of the galactopyranosyl derivative:

1,2,3,4,6-O-pentaacetyl-β-D-galactopyranose (3.9 g, 10 mmol) was synthesized by reacting D(+)galactose (20 g, 0.11 mol) with acetic anhydride (140.4 g, 1.376 mol) in pyridine (95 mL) at 10° C. for 72 hours. It was then condensed (Helferich glycosidation method) with 2,3,5-triiodobenzyl alcohol (4.85 g, 10 mmol) and para-toluene sulfonic acid monohydrate (5.0 g, 26.3 mmol) in dimethylformamide (30 mL) at 85°-90° C. for 24 hours. After removal of the residual O-acetyl groups using a catalytic amount of sodium methoxide (200 mg, 3.7 mmol) in methanol (20 mL, 25° C., 2 hours), the anomeric mixture of 1-O-(2,3,5-triiodobenzyl)-D-galactopyranoside is isolated by recrystallization from 2-propanol.

C. Preparation of the 4-O--D-galactopyranosyl-alpha-D-glucopyranosyl derivative:

2,3,4,6-O-tetraacetyl-D-galactosyl-1,2,3,5-O-tetraacetyl-alpha-D-glucopyranoside (6.78 g, 10 mmol), synthesized by reacting alpha-D-lactose (20.0 g, 58.4 mmol) with acetic anhydride (80 mL, 86 g, 0.85 mol) in pyridine (60 mL) at 10° C. for 72 hours, is condensed with 2,3,5-triiodobenzyl alcohol (4.85 g, 10 mmol) and para-toluene sulfonic acid monohydrate (5.0 g, 26.3 mmol) in dimethylformamide (30 mL) at 85°-90° C. for 24 hours. After removal of the residual O-acetyl groups using a catalytic amount of sodium methoxide (200 mg, 3.7 mmol) in methanol (20 mL, 25° C., 2 hours), the anomeric mixture of 1-O-(2,3,5-triiodobenzyl)-4-O-D-galactopyranosyl-D-glucopyranoside is isolated by recrystallization from 2-propanol.

What is claimed is:

1. A method for X-ray imaging a specific population of cells in an animal comprising:
   (i) forming a complex of a radiopaque label with a saccharide capable of being bound to a cell receptor and further being capable of being internalized by said cell via receptor mediated endocytosis;
   (ii) administering to the animal a diagnostically effective amount of this complex;
   (iii) forming an X-ray image of the animal.

2. A method according to claim 1, wherein the saccharide is a polysaccharide that is selected from the group consisting of arabinogalactan, mannose, degradation products of any of the foregoing and derivatives of any of the foregoing.

3. A method according to claim 2, wherein the polysaccharide is arabinogalactan modified with organic linking groups.

4. A method according to claim 3, wherein the organic linking group is selected from the group consisting of an aminopolycarboxylic acid, a polycarboxylic acid, a polyamine and an aminoalkanol.

5. A method according to claim 4, wherein the organic linking group is selected from the group consisting of diethylenetriaminepentaacetic acid, succinic acid, glutaric acid, ethylenediamine and aminoethanol.

6. A method according to claim 2, wherein the radiopaque label includes a compound containing iodine.

7. A method according to claim 6, wherein the radiopaque label is selected from the group consisting of a polyiodinated aromatic group and a polyiodinated aliphatic group.

8. A method according to claim 7, wherein the radiopaque label includes a compound selected from the group consisting of ioversol, metrizoic acid and 3-amino-2,4,6-triiodobenzoic acid.

9. A method according to claim 4, wherein the radiopaque label includes a compound containing iodine.

10. A method according to claim 9, wherein the radiopaque label is selected from the group consisting of a polyiodinated aromatic group and a polyiodinated aliphatic group.

11. A method according to claim 10, wherein the radiopaque label includes a compound selected from the group consisting of ioversol, metrizoic acid and 3-amino-2,4,6-triiodobenzoic acid.

12. A method according to claim 5, wherein the radiopaque label includes a compound containing iodine.

13. A method according to claim 12, wherein the radiopaque label is selected from the group consisting of a polyiodinated aromatic group and a polyiodinated aliphatic group.

14. A method according to claim 13, wherein the radiopaque label includes a compound selected from the group consisting of ioversol, metrizoic acid and 3-amino-2,4,6-triiodobenzoic acid.

15. A method according to claim 1, wherein the saccharide is attached to a compound that is incapable of performing receptor mediated endocytosis, providing a complex of the composition and the saccharide, wherein the resulting complex is capable of interacting with a cell receptor and performing receptor mediated endocytosis.

16. A method according to claim 1, wherein the saccharide is galactose.

17. A method according to claim 16, wherein the saccharide is galactose modified with organic linking groups.

18. A method according to claim 17, wherein the radiopaque label includes 2,3,5-triiodobenzyl alcohol.

* * * * *

UNITED STATES PATENT AND TRADEMARK OFFICE
CERTIFICATE OF CORRECTION

PATENT NO. : 5,141,739

DATED : August 25, 1992

INVENTOR(S) : Chu Jung, et al.

It is certified that error appears in the above-indentified patent and that said Letters Patent is hereby corrected as shown below:

col. 1, line 5:  immediately after the title of the invention, the following sentence should be added:

"Under 35 USC 202(c)(6) the government may have certain rights in the inventions claimed in this patent, based upon support that it provided to the applicants and their assignee."

Signed and Sealed this

Thirtieth Day of August, 1994

Attest:

BRUCE LEHMAN

Attesting Officer

Commissioner of Patents and Trademarks